United States Patent [19]
Kataoka et al.

[11] 4,065,362
[45] Dec. 27, 1977

[54] PURIFICATION OF ORGANIC ISOCYANATES

[75] Inventors: Yushin Kataoka; Tetsuo Harada; Kenji Takagi, all of Niihama, Japan

[73] Assignee: Sumitomo Bayer Urethane Co., Ltd., Japan

[21] Appl. No.: 582,803

[22] Filed: June 2, 1975
(Under 37 CFR 1.47)

[30] Foreign Application Priority Data
June 4, 1974  Japan .................................. 49-63592

[51] Int. Cl.$^2$ .............................................. B01D 3/34
[52] U.S. Cl. ........................................ 203/58; 203/59;
203/65; 203/60; 260/453 SP; 203/38
[58] Field of Search ................. 260/453 SP; 203/6, 8, 203/9, 60, 65, 38, 58, 59

[56] References Cited
U.S. PATENT DOCUMENTS

| | | | |
|---|---|---|---|
| 2,957,903 | 10/1960 | Spiegler | 260/453 SP |
| 3,055,078 | 5/1962 | DeLong et al. | 260/453 SP |
| 3,458,558 | 7/1969 | Cheng | 260/453 SP |
| 3,660,456 | 5/1972 | Naito et al. | 260/453 SP |
| 3,715,381 | 2/1973 | Spaunburgh et al. | 260/453 SP |

*Primary Examiner*—Norman Yudkoff
*Attorney, Agent, or Firm*—Connolly and Hutz

[57] ABSTRACT

The present invention provides a process for purifying an organic isocyanate which comprises heating an organic isocyanate in admixture with a treating agent selected from the group consisting of a metal salt of mercaptobenzothiazol, a dithiocarbamic acid derivative, an alkyl-substituted phenol, a thio-bisphenol, and a triaryl phosphite at a temperature not lower than 100° C and subsequently distilling the thusly treated mixture to recover a purified organic isocyanate.

21 Claims, No Drawings

PURIFICATION OF ORGANIC ISOCYANATES

This invention relates to a process for purifying organic isocyanates which comprises heating an organic isocyanate in contact with a treating agent selected from the group consisting of a metal salt of mercapto benzothiazole, a dithiocarbamic acid derivative, an alkyl substituted phenol, a thio-bisphenol and a triaryl phosphite at a temperature of at least 100° C and distilling the treated mixture to recover a purified organic isocyanate, It is well known in the art that organic isocyanates especially organic polyisocyanates, are generally colorless liquid or solid and that they are very reactive substances which due to their high reactivity and lability show a strong tendency to discoloration upon storage. Most probably this discoloration upon storage is due to impurities of unknown nature.

It is, therefore, of highest interest to provide methods for purification and color stabilization of organic isocyanates which are to be used for the preparation of polyurethane plastics.

Various processes for this purpose have been suggested. Thus, for example, Japanese patent Publications Sho-42-17887, 42-26767, 43-30211, or 46-17220 propose a treatment of the organic isocyanates with copper, aluminum or iron compounds prior to distillation. These methods of the art permit reduction of the content of hydrolysible chlorine components in the organic isocyanates but are not satisfactory as far as color stabilization is concerned. This is obviously due to the fact that these methods of the art do not permit to removal of the impurities which are responsible for the phenomenon of discoloration upon storage.

The present invention provides a new method for the purification and color stabilization of organic isocyanates which comprises contacting the organic isocyanate at high temperatures with specific organic compounds specified hereinafter and subsequently distilling the thusly treated isocyanate.

Organic isocyanates which can be stabilized according to the process of this invention are for example those of the formula $$R(NCO)_n$$

wherein

R stands for a saturated aliphatic hydrocarbon radical having 4 to 12 carbon atoms, a saturated cycloaliphatic hydrocarbon radical having from 5 to 15 carbon atoms, an aromatic hydrocarbon radical having from 6 to 15 carbon atoms, or an araliphatic hydrocarbon radical having from 7 to 15 carbon atoms, and n stands for an integer of from 1 to 3.

Specific examples of such isocyanates are 4,4'-diisocyanato diphenylmethane, hexamethylene diisocyanate, tetramethylene diisocyanate, phenyl isocyanate, meta-xylylene diisocyanate, para-xylylene diisocyanate, 4,4'-diphenylether diisocyanate, 1,4-phenylene diisocyanate, 1,5-naphthalene diisocyanate, 2,4-diisocyanato toluene, 2,6-diisocyanato toluene, 4,4'-diisocyanato diphenyl ethane, triphenyl methane diisocyanate. The process of this invention is particularly suitable for the purification and color stabilization of 4,4'-diisocyanato diphenyl methane.

The treating agents used in accordance with the present invention are selected from the group consisting of a metal salt of mercapto benzothiazole, a dithiocarbamic acid derivative, an alkyl substituted phenol, a thiobis-phenol, and a triaryl phosphite.

A metal salt of mercapto benzothiazole used in the present invention is a compound of the structure

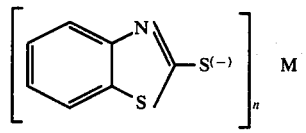

wherein M stands for A cation of a metal of group I, group II or group VIII of the Periodic Table of Elements, preferably sodium, potassium, copper, silver, calcium, strontium, zinc, cadmium, mercury, iron, cobalt, nickel ruthenium or palladium, more preferably M is metal cation of sodium, potassium, zinc, cobalt, nickel or copper, and wherein n stands for an integer that corresponds to the valency of metal ion, preferably 1–3. Specific examples for such compounds are zinc mercaptobenzothiazole, cupric mercaptobenzothiazole, nickel mercaptobenzothiazole, sodium mercaptobenzothiazole, potasium mercaptobenzothiazole, or cobalt mercaptobenzothiazole.

A dithiocarbamic acid derivative suitable for the process of the present invention is a compound having the structure

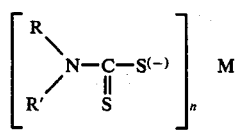

wherein R is an unsubstituted alkyl group having 1 to 10, preferably 1 to 4 carbon atoms or an aryl group having the following general formula

(wherein R'' and R''' are each hydrogen atom or unsubstituted alkyl groups having 1 to 5 carbon atoms); R' is an unsubstituted alkyl groups having 1 to 10, preferably 1 to 4 carbon atoms; M is a cation of a metal atom of group I, group II, group VI or group VIII of the Periodic Table of Elements preferably sodium, potassium, copper, silver, calsium, strontium, zinc, cadmium, mercury, chromium, selenium, tellurium, iron, cobalt, nickel, ruthenium or palladium, more preferably M is metal cation of zinc, sodium, potassium or nickel; and wherein n stands for an integer that corresponds to the valency of the metal ion, preferably 1—3.

Specific examples for such compounds are zinc dimethyldithiocarbamate, sodium dimethyldithiocarbamate, zinc diethyldithiocarbamate, potasium dibutyldithiocarbamate, sodium dibutyldithiocarbamate, nickel dibutyldithiocarbamate, zinc dibutyldithiocarbamate, or zinc ethylphenyl dithiocarbamate.

Alkyl substituted phenols suitable for the process of the present invention are especially dialkyl phenols or trialkyl phenols of the formula

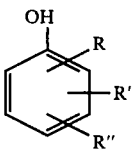

wherein at least two preferably all three of the radicals R,R', a and R" are unsubstituted alkyl groups having 1 to 20 preferably 1 to 12 and most preferably 1 to 4 carbon atoms and wherein the third radical may also stand for hydrogen. At least one of said alkyl radicals are substituted at the ortho-position to the hydroxyl group. Specific examples for such compounds are 2,4-diisopropyl-5-methyl phenol, 2,4-dimethyl-6-t-butyl phenol, 2,6-di-t-butyl-4-methyl phenol, 2,6-di-t-butyl phenol, 2,6-di-n-dodecyl-4-methyl phenol, 2,4,6-tridecyl phenol, 2,6-didecyl-4-t-butyl phenol.

Thiobis-phenols suitable for the process of the invention are preferably thiobis-(dialkylphenols) having the following general formula

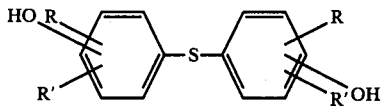

wherein R and R' each stand for an unsubstituted alkyl group having from 1 to 10, preferably from 1 to 4 carbon atoms, at least one alkyl group being preferably in ortho-position to each of the phenolic hydroxyl groups. Specific examples for such compounds are 2,2'-thiobis (4-methyl-6-t-butyl phenol), 4,4'-thiobis-(6-t-butyl-3-methyl phenol) and 4,4'-thiobis-(6-t-butyl-2-methyl phenol).

Triaryl phosphites suitable for the process of the present invention have the structure.

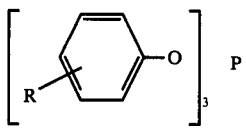

wherein R stands for hydrogen or an unsubstituted alkyl group having form 1 to 20, preferably from 1 to 10 most preferably from 1 to 4 carbon atoms.

Specific examples for such compounds are triphenyl phosphite, tri (o-cresyl) phosphite, tri (p-cresyl) phosphite, trioctylphenyl phosphite, tridecylphenyl phosphite and trinonylphenyl phosphite.

The preferred compounds used in the process of the present invention are zinc or cupric salts of mercaptobenzothiazole, 2,4-dimethyl-6-t-butylphenol, 2,6-t-butyl-4-methyl phenol, 4,4'-thiobis (6-t-butyl-3-methyl phenol), 4,4'-thiobis (6-t-butyl-2-methyl phenol), nickel dibutyl dithiocarbamate, zinc dimethyl dithiocarbamate, triphenyl phosphite and tri (o-cresyl) phosphite.

These treating agents agents can be used alone or in admixture in this invention.

The amount of the treating agent used in the present invention may be usually from about 0.001 to about 5% by weight, preferably 0.005 to 1% by weight, based on the weight of the starting organic isocyanate.

When less than 0.001% by weight of the treating agents to organic isocyanate is used for the treatment, removal of coloring impurities from organic isocyanate is not enough. On the other hand, when organic isocyanate is treated with more than 5% by weight of the treating agents, much more amount of tarry matter is formed and organic isocyanate is lost considerably. Therefore, generally,, the above mentioned amount of treating agents is used.

The treatment of organic isocyanate in the present invention may be carried out at an elevated temperature. The heat treatment is performed generally at a temperature not lower than 100° C, preferably at a temperature from 150° to 250° C. Heat treatment at lower than 100 C, treatment effect for purification is not satisfying.

The time of heat treatment varies depending upon the treating agent, an amount of addition, treatment temperature, a starting organic isocyanate, and generally, the treatment time is 0.1 to 10 hours but is not limited to this range. The heat treatment can also be performed in an inert solvent against organic isocyanate such as n-hexane, toluene, monochlorobenzene, o-dichlorobenzene, p-dichlorobenzene, trichlorobenzene, chlorinated toluenes, chlorinated xylenes, chloroethylbenzene, benzene said and xylene. The thus treated organic isocyanate is distilled and the purified organic isocyanate is recovered having excellent color stability. The distillation can be carried out under normal pressure and also at reduced pressure.

The reason why organic isocyanate treated according to the present invention shows excellent color stability is not clear but it might be considered that coloring impurities are converted into tar selectively by the heat treatment in the presence of the specified treating agents used in this invention.

By the above described process of this invention, all or substantially all of the coloring impurities are converted into tar and the tar is removed from organic isocyanate as distillation residue, consequently, organic isocyanate treated and recovered by the process of this invention shows excellent storage stability.

Therefore, thusly obtained organic isocyanate may be used without any trouble for applications such as fiber for which excellent quality of raw material is absolutely required.

Practical and presently preferred embodiments of the present invention are illustratively shown in the following Examples.

EXAMPLE 1

150 g of raw 4,4'-methylene-bis-(phenylisocyanate) was put into $N_2$ gas-substituted flask having an agitator and cooler. And the desired quantity of treating agent shown in Table I was added. The mixture was heated and agitated under $N_2$ gas sealing and under the conditions shown in Table I. After heat-treatment and agitation, reactants were distilled under 1 to 2 mm Hg pressure and pure 4,4'-methylene-bis-(phenylisocyanate) was recovered. Produced pure 4,4'-methylene-bis-(phenylisocyanate) was left at room temperature under air sealing for a week and its color stability was checked. The result is shown in Table I.

Table I

| | Exp. No. | Agents | Addition amount (weight % to organic isocyanate) | Treatment condition temperature (° C) | Treatment condition time (hours) | Color stability (APHA)* |
|---|---|---|---|---|---|---|
| Example | 1 | Zinc mercaptobenzothiazole | 0,1 | 200 | 3 | 10 |
| | 2 | Cupric mercaptobenzothiazole | 0,05 | 220 | 1 | 10 |
| | 3 | Zinc dimethyldithiocarbamate | 0,1 | 210 | 2 | 20 |
| | 4 | Nickel dibutyldithiocarbamate | 0,2 | 210 | 1 | 20 |
| | 5 | 2,6-di-t-butyl-4-methylphenol | 0,05 | 220 | 2 | 10 |
| | 6 | 2,4-dimethyl-6-t-butylphenol | 0,1 | 210 | 3 | 20 |
| | 7 | 4,4'-thiobis-(6-t-butyl-2-methylphenol) | 0,05 | 220 | 2 | 10 |
| | 8 | 4,4'-thiobis-(6-t-butyl-3-methylphenol) | 0,3 | 200 | 3 | 10 |
| | 9 | Triphenylphosphite | 0,2 | 210 | 2 | 20 |
| | 10 | Tri (o-cresyl) phosphite | 0,1 | 220 | 1 | 20 |
| | 11 | Zinc mercaptobenzothiazole + 4,4'-thiobis-(6-t-butyl-3-methylphenol) | 0,02 0,03 | 210 | 2 | 10 |
| | 12 | Cupric mercaptobenzothiazole + 2,6-di-t-butyl-4-methylphenol | 0,03 0,05 | 220 | 1 | 10 |
| Compared example | 13 | — | — | — | — | 400 |
| | 14 | — | — | 220 | 3 | 400 |
| | 15 | 2,6-di-t-butyl-4-methylphenol | 0,5 | 80 | 4 | 400 |
| | 16 | ferric chloride | 0,1 | 220 | 3 | 400 |

*APHA Method (in accordance with ASTM D 1209-62)

EXAMPLE 2

In the same manner as in Example 1, toluene diisocyanate was treated with the treating agents and under the conditions shown in Table II and the purified toluene diisocyanate was obtained after distillation. The color stability of the purified toluene diisocyanate at room temperature and under air sealed condition was checked. The results after 7 days storage are shown in Table II.

EXAMPLE 3

In the same manner as described in Example 1, hexamethylene diisocyanate was treated with the treating agent and under the conditions shown in Table III. And the purified hexamethylene diisocyanate was obtained after distillation. The color stability of the purified hexamethylene diisocyanate at room temperature and under air sealed condition was checked. The result after 7 days storage is shown in Table III.

TABLE II

| Experiment No. | Agents | Addition amount (weight % to organic isocyanate) | Treatment condition Temperature (° C) | Treatment condition Time (Hours) | Color Stability (APHA)* |
|---|---|---|---|---|---|
| Example 17 | Zinc mercaptobenzothiazole | 0,2 | 150 | 4 | 30 |
| Example 18 | 2,6-t-butyl-4-methylphenol | 0,1 | 200 | 1 | 20 |
| Compared example 19 | — | — | — | — | 100 |

*APHA Method (in accordance with ASTM D 1209-62)

TABLE III

| Experiment No. | Agents | Addition amount (weight % to organic isocyanate) | Treatment condition Temperature (° C) | Treatment condition Time (Hours) | Color Stability (APHA)* |
|---|---|---|---|---|---|
| Example 20 | 4,4'-thiobis-(6-t-butyl-3-methylphenol) | 0,1 | 200 | 2 | 20 |
| Compared example 21 | — | — | — | — | 100 |

*APHA Method (in accordance with ASTM D 1209-62)

From the results shown in Table I, II, and III it is clear that organic isocyanate treated by the method of this invention has excellent color stability.

What we claim is:

1. A process for purifying an organic isocyanate which comprises heating an organic isocyanate in admixture with at least one treating agent selected from the group consisting of a metal salt of mercaptobenzothiazol, a metal salt of alkyl substituted dithiocarbamic acid, an alkyl substituted phenol, a thio-bis-phenol, and a triaryl phosphite at a temperature not lower than 100° C. to thereby convert coloring impurities to tar and subsequently distilling the thusly treated mixture to recover a purified organic isocyanate.

2. The purified organic isocyanate produced by the process of claim 1.

3. The process of claim 1 wherein said organic isocyanate is of the formula $$R(NCO)_n$$

wherein R is selected from the group consisting of saturated aliphatic hydrocarbon having 4 to 12 carbon atoms, saturated cycloaliphatic hydrocarbon having from 5 to 15 carbon atoms, aromatic hydrocarbon having from 6 to 15 carbon atoms and araliphatic hydrocarbon having from 7 to 15 carbon atoms and n is an integer of from 1 to 3.

4. The process of claim 1 wherein said organic isocyanate is selected from the group consisting of 4,4'-diisocyanato diphenylmethane, hexamethylene diisocyanate, tetramethylene diisocyanate, phenyl isocyanate, meta-xylylene diisocyanate, para-xylylene diisocyanate, 4,4'-diphenylether diisocyanate, 1,4-phenylene diisocyanate, 1,5-naphthalene diisocyanate 2,4-diisocyanato toluene, 2,6-diisocyanato toluene, 4,4'-diisocyanato diphenyl ethane and triphenyl methane diisocyanate.

5. The process of claim 1 wherein said organic isocyanate is 4,4'-diisocyanato diphenyl methane.

6. The process of claim 1 wherein said treating agent is a metal salt of mercaptobenzothioazole of the formula

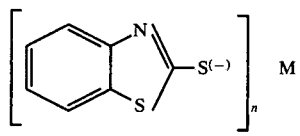

wherein M is a cation of a metal of Group I, II or VIII of the Periodic Table of Elements.

7. The process of claim 6 wherein said metal salt is selected from the group consisting of zinc mercaptobenzothioiazole, cupric mercaptobenzothiazole, nickel mercaptobenzothiazole, sodium mercaptobenzothiazole, potassium mercaptobenzothiazole and cobalt mercaptobenzothiazole.

8. The process of claim 1 wherein said treating agent is a metal salt of alkyl substituted dithiocarbamic acid of the formula

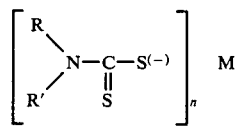

wherein R' is alkyl having 1 to 10 carbon atoms; M is a cation of a metal of Group I, II, VI or VIII of the Periodic Table of Elements, n is an integer corresponding to the valence of M and R is alkyl having 1 to 10 carbon atoms or

wherein R" and R'" are hydrogen or alkyl having 1 to 5 carbon atoms.

9. The process of claim 8 wherein said metal salt is selected from the group consisting of zinc dimethyldithiocarbamate, sodium dimethyldithiocarbamate, zinc dimethyldithiocarbamate potassium dibutyldithiocarbamate, sodium dibutyldithiocarbamate, nickel dibutyldithiocarbamate, zinc dibutyldithiocarbamate and zinc ethylphenyl dithiocarbamate.

10. The process of claim 1 wherein said alkyl substituted phenol is of the formula

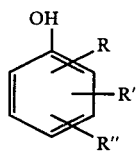

wherein R and R' are alkyl having 1 to 20 carbon atoms and R" is selected from the group consisting of hydrogen and alkyl having 1 to 20 carbon atoms.

11. The process of claim 10 wherein said alkyl substituted phenol is selected from the group consisting of 2,4-diisopropyl-5-methyl phenol, 2,4-dimethyl-6-t-butyl phenol, 2,6-di-t-butyl-4-methyl phenol, 2,6-di-t-butyl phenol, 2,6-di-n-dodecyl-4-methyl phenol, 2,4,6-tridecyl phenol and 2,6-didecyl-4-t-butyl phenol.

12. The process of claim 1 wherein said treating agent is a thiobis-phenol of the formula

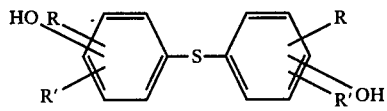

wherein R and R' are each alkyl having from 1 to 10 carbon atoms.

13. The process of claim 12 wherein said thiobisphenol is selected from the group consisting of 2,2°-thiobis (4-methyl-6-t-butyl phenol), 4,4'-thiobis-(6-t-butyl-3-methyl phenol) and 4,4'-thiobis-(6-t-butyl-2-methyl phenol).

14. The process of claim 1 wherein said treating agent is triaryl phosphite of the formula

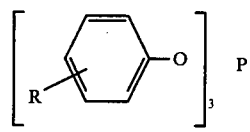

wherein R is hydrogen or alkyl having from 1 to 20 carbon atoms.

15. The process of claim 14 wherein said triaryl phosphite is selected from the group consisting of triphenyl phosphite, tri (o-cresyl) phosphite, tri (p-cresyl) phosphite, trioctylphenyl phosphite, tridecylphenyl phosphite and trinonylphenyl phosphite.

16. The process of claim 1 wherein said treating agent is selected from the group consisting of zinc mercaptobenzothiazole, cupric mercaptobenzothiazole, 2,4-dimethyl-6-t-butylphenol, 2,6-t-butyl-4-methyl phenol, 4,4'-thiobis (6-t-butyl-3-methyl phenol), 4,4'-thiobis (6-t-butyl-2-methyl phenol), nickel dibutyl dithiocarbamate, zinc dimethyl dithiocarbamate, triphenyl phosphite and tri (o-cresyl) phosphite.

17. The process of claim 1 wherein said treating agent is present in an amount of about 0.001 to about 5% by weight, based on the weight of organic isocyanate.

18. The process of claim 1 wherein said heating step is carried out at a temperature of from 150° to 250° C.

19. The process of claim 1 wherein said heating step is carried out for from 0.1 to 10 hours.

20. The process of claim 1 wherein said heat treatment is carried out in the presence of an inert organic solvent selected from the group consisting of n-hexane, toluene, monochlorobenzene, o-dichlorobenzene, p-dichlorobenzene, trichlorobenzene, chlorinated toluenes, chlorinated xylenes, chloroethylbenzene, benzene and xylene.

21. The purified organic isocyanate produced by the process of claim 1 wherein said organic isocyanate is selected from the group consisting of 4,4'-diisocyanato diphenylmethane, hexamethylene diisocyanate, tetramethylene diisocyanate, phenyl isocyanate, meta-xylylene diisocyanate, para-xylylene diisocyanate, 4,4'-diphenylether diisocyanate, 1,4-phenylene diixocyanate, 1,5-naphthalene diisocyanate 2,4-diisocyanato toluene, 2,6-diisocyanato toluene, 4,4'-diixocyanato diphenyl ethane and triphenyl methane diisocyanate.

* * * * *